United States Patent [19]
Salkin

[11] Patent Number: 5,948,824
[45] Date of Patent: Sep. 7, 1999

[54] USE OF A CHEMICAL AGENT FOR REDUCING THE CHANGES IN WAISTLINE AND THE EFFECT OF CONSTIPATION DUE TO THE TAKING OF OTHER AGENTS

[76] Inventor: André Salkin, 134 Avenue du 14 Juillet, 76300 Sotteville les Rouen, France

[21] Appl. No.: 08/965,964

[22] Filed: Nov. 7, 1997

[30] Foreign Application Priority Data

Nov. 8, 1996 [FR] France ................................ 96 13646
Jun. 20, 1997 [FR] France ................................ 97 07693
Jul. 28, 1997 [FR] France ................................ 97 09559
Jul. 30, 1997 [FR] France ................................ 97 09701

[51] Int. Cl.$^6$ ........................... A61K 45/08; A61K 47/44
[52] U.S. Cl. ................. 514/769; 514/770; 514/772.5; 514/892; 514/922; 514/949; 424/78.01; 424/78.32
[58] Field of Search .................... 514/769, 770, 514/772.5, 892, 922, 949; 424/78.01, 78.32

[56] References Cited

U.S. PATENT DOCUMENTS 5,418,220  5/1995  Schmidt et al. ........................ 514/63

FOREIGN PATENT DOCUMENTS 0273209   7/1988  European Pat. Off. .
8198761   8/1996  Japan .
WO9517201 6/1995  WIPO .

*Primary Examiner*—Frederick Krass
*Attorney, Agent, or Firm*—Dennison, Meserole, Scheiner & Schultz

[57] ABSTRACT

The invention relates to the use of a chemical agent of organic origin for reducing or eliminating changes in waistline or for reducing or eliminating constipation due to the taking of other agents. A preferred agent is a polyvinylpyrrolidone or povidone. By virtue of the invention, changes in waistline are reduced or eliminated during the day, as well as constipation which can be generated by the taking of other agents such as clays.

22 Claims, No Drawings

5,948,824

USE OF A CHEMICAL AGENT FOR REDUCING THE CHANGES IN WAISTLINE AND THE EFFECT OF CONSTIPATION DUE TO THE TAKING OF OTHER AGENTS

Use of a chemical agent reducing the changes in waistline and the effect of constipation due to the taking of other agents.

The invention relates to the use of at least one organic chemical compound for reducing or making changes in waistline disappear during the day.

The invention also relates to a induction of the constipating effect of certain chemical compounds.

Eating habits and life-styles in industrial countries promote physiological malfunctioning, and imbalances.

The present inventor has been able to observe that the result of these disorders for the subjects concerned, and more particularly for male or female city-dwellers, is a change in waistline during the day, the consequence, of which is a sensation of compression in clothes, skirts or trousers.

The present invention has been able to observe that certain agents which promote the reduction of the waistline produced an undesirable constipating effect.

Thus, the object of the present invention is to provide solutions which enable reducing or eliminating changes in waistline, while at the same time suppressing the effects in question.

The invention provides a novel solution, which is technically reliable and satisfactory on an industrial scale, in the field of the production either of comfort products, dietary supplements, or food products which do not promote changes in waistline.

The value of this novel solution resides in the fact that it is completely harmless to the organism.

Thus, according to a first aspect, the invention relates to the use of at least one chemical agent, of organic origin, for reducing the effects of change in waistline, due to the life-style and eating habits of people in industrialised countries.

According to a second aspect, the invention also relates to the use of a polyvinylpyrrolidone or povidone, in particular a soluble or insoluble, cross-linked or non cross linked polyvinylpyrrolidone or povidone having a molecular weight between 10,000 and more than 2.8 million, for reducing or eliminating changes in waistline.

According to a third aspect, the invention also relates to the use of a polyvinylpyrrolidone or povidone, in particular a soluble or insoluble cross-linked or non-cross-linked polyvinylpyrrolidone or povidone having a molecular weight between 10,000 and more than 2.8 million, for reducing the effect of constipation due to the taking of certain agents such as activated charcoal and clay.

Polyvinylpyrrolidone (PVP) is also called povidone in The Merck Index, 9th Edition, page 996, No. 7498. These two terms are therefore equivalent within the context of the present invention. The term polyvinylpyrrolidone groups together every polyvinylpyrrolidone, in particular soluble or insoluble, cross-linked or non-cross-linked polyvinylpyrrolidones having a molecular weight between 10,000 and more than 2.8 million. The insoluble polyvinylpyrrolidones are sometimes also called polyvinylpolypyrrolidones. From this, the invention also covers polyvinylpolypyrrolidones. Such polyvinylpyrrolidones or polyvinylpolypyrrolidones are available, notably from GAF®, an American company, under the designation Plasdone® for the soluble polyvinylpyrrolidones, and Polyplasdone® for the insoluble polyvinylpyrrolidones or polyvinylpolypyrrolidones.

According to another advantageous embodiment, the agent is present in the form of a distinct composition for separately absorbing foods.

According to another advantageous embodiment, the above-mentioned agent is incorporated directly in one or more foods.

The agent can be formulated as various galenic forms. Such galenic forms and the methods of preparing them are familiar to the person skilled in the art.

According to another advantageous embodiment of the invention, the concentration of the above mentioned agent is between a homeopathic concentration and 100% by weight or by volume.

According to another embodiment, it will be possible for the agent in question, i. e. preferably PVP, to be formulated in a synergetic association with another compound selected from the group consisting of an activated charcoal, a clay, preferably a montmorillonite, kaolinite, attapulgite, sepiolite, smectite and bentonite clay. It has proved to be that the preparations containing PVP in association with one or more active compounds mentioned above produced synergetic effects while at the same time reducing the cost price.

PVP is already used in food compositions as an additive having a firming or stabilising tehnological effect (SIN: 1201).

According to the patent of the same Applicant registered at the French Patent Office (the INPI) under the number 9603276 and published under the number 2,745,981, PVP may be used in a mixture in food composition, for reducing or eliminating the side-effects due to the taking of sweetening agents. These effects are, for example, electrolytic disorder, diarrhoea and sensations of digestive torsion.

PVP has also been used in therapeutics and has received marketing authorisations as a medicament, especially in the case of enterogastric illnesses. The known medicament is found particularly in France under the MA numbers 307 529.2 and 314 449.0.

In the enterogastric field, many other medicaments exists which are based on proton pump inhibitors, prostaglandins, topical anti-ulcer agents, locally acting antacids. These medicaments can also comprise clay, activated charcoal, polyvinylpyrrolidone, silicones and even other available molecules. These medicaments are found in France under the MA numbers: 319 230.7/319 231.3/322 970.8/ 322 971.4/300 071.0/300 072.7/330 605.5/300 606.1/329 851.4/ 330 869.0. The point in common or all these products is to treat illnesses.

In contrast, within the context of the present invention, the development of a comfort product is sought. The object is to principally treat the bolus in order that it is not at the origin of disorders and malfunctioning which increase changes in waistline.

Within the context of the present invention, it is also sought to reduce the constipating effects of other agents, such as clays, which have already been used in the field of digestive disorders.

The invention also covers a composition, such as a food or drink composition, characterised in that it contains at least one chemical agent of organic origin, preferably polyvinylpyrrolidone or povidone, in an amount effective for reducing or suppressing changes in waistline.

According to another aspect, the invention relates to a composition, such as a food or drink composition, characterised in that it contains at least one chemical agent of organic origin, preferably polyvinylpyrrolidone or povidone, in a synergetic association with another agent, clay in particular, in an amount effective for reducing or eliminating chances in waistline and constipation due to the taking of the other agent.

A further object of the present invention is compositions whose active principle component will be at least one chemical agent of organic origin mentioned above, preferably PVP, alone or in a synergetic association with other active compounds such as charcoal or clay, the concentration of the agent, preferably PVP, ranging between a homeopathic concentration and 100% by weight or by volume, it being possible for the other components to be of concentration from 99.9% a 0%. These compositions will be presented either as various galenic forms (capsules, tablets, pills, granules), or in the form of anti-change-in-waistline foods such as drinks, salad oils, drinking water, or chewing gum.

The invention also relates to a method of treating the bolus, characterised in that it comprises the administration, to a human being eating said bolus, at the same time as or separate from said bolus, an effective amount of at least one chemical agent, preferably polyvinylpyrrolidone or povidone, formulated alone or in a synergetic association with other agents such as activated charcoal, clay, preferably a clay selected from a montmorillonite, kaolinite, attapulgite, sepiolite, smectite and bentonite clay, for reducing or suppressing changes in waistline, or for reducing the constipating effects of such other agents and in particular clays.

For any one of the aspects of the invention, at least one chemical agent of organic origin mentioned above, advantageously a polyvinylpyrrolidone or polyvinylpolypyrrolidone, can be used at a concentration ranging from a homeopathic concentration up to 100% by weight or by volume according to whether the composition is solid or liquid. An advantageous concentration is about at least $10^{-12}$ g to 100% by weight or by volume of the composition or bolus, to be taken separately or preferably incorporated directly in one or more foods. A more preferable dose will be of the order of $10^{-12}$ g to 1 g per unit dose, or for 100 g of product to be chewed, such as chewing gum, or to be consumed.

The invention can be formulated as various galenic forms such as capsules, tablets or granules in a mixture in food compositions such as drinkable or sweet compositions, food oil compositions, drinking water, chewing gum, and the Examples given hereinafter make up an integral part of the present invention, in the most general characteristics.

Other aims, characteristics and advantages of the invention will appear clearly to the person skilled in the art from the following description made with reference to several Examples of realisation which are given simply in an illustrative way, and therefore in no way limit the scope of the invention. In the Examples, all proportions are given by weight unless otherwise stated.

EXAMPLE 1
PVP Formulated as Various Galenic Forms
PVP is the sole active compound, formulated as tablets, capsules or granules.
a) Capsule Case
Capsules are prepared in a conventional manner which contain, per capsule, about 0.1 g of polyvinylpyrrolidone, for example Plasdone® K29-32 or Polyplasdone INF 10 available from GAF®, USA, which is presented in the form of a powder. The composition of the capsule is conventional and can, for example, be made from gelatine.

Up to 6 capsules may be taken per day, before or after main meals, such that 0.3 to 0.6 g of polyvinylpyrrolidone is provided whose presence in the body will enable reducing or eliminating changes in waistline caused by eating habits.

b) Tablets Case
In the case, the polyvinylpyrrolidone can be mixed with a conventional powder excipient, and then compressed into tablet. The excipient that can be used is any food-or medically-acceptable excipient, such as gelatine or magnesium stearate. In this context, the proportion of PVP in the tablet will be such that an amount of the order 0.05 g to 3 g per day is provided, either in one tablet or in several tablets.

c) Granules Case
The granules may be formulated to be easily swallowed with a little water. In this case, the PVP may or may not be associated with an excipient, then a grain may be produced via the dry route or the moist route. Within the context of a dosage, for example of 0.5 g per day, a sachet of 5 g of granules containing 0.5 g of PVP can be prepared.

EXAMPLE 2
PVP Formulated in a Mixture in Food Compositions
a) Sweet Drinkable Composition
The PVP according to the invention may be incorporated right from the initial formulation of the drinkable compositions. These are drinkable compositions which are sweet or which contain sweetening agents other than sugar.

For example, in a Coke®-based drink, 1 g of Plasdone K29-32 or K90 commercially available from GAF®. USA, will be Incorporated by simple mixing during its manufacture.

b) Food Oil Composition
In this case, the PVP is incorporated in a mixture after the extraction phase. For example, 2 grams of PVP will be incorporated for 1 liter of salad oil.

c) Incorporation in Drinking Water
The PVP may be added directly to drinking water. 0.5 g of Polyplasdone INF 10, available from GAF®. USA, can be mixed with 1 liter of mineral water before bottling.

d) Chewing Gum Composition
In a classical chewing gum composition, 0.5 g of PVP and 0.2 g of montmorillonite clay will be added for 100 g of chewing plate.

COMPARATIVE TESTS DEMONSTRATING
THE REDUCTION OF CHANGES IN
WAISTLINE AND CONSTIPATION BY TAKING
PVP ACCORDING TO THE INVENTION AFTER
MEALS

EXAMPLE 3
PVP Formulated in a Preparation with Montmorillonite Clay
Tablets containing 30 mg of PVP and 50 mg of montmorillonite of average particle size of the order of 20 μm, and tablets containing 300 mg of montmorillonite are prepared according to the invention. Placebos are prepared by replacing the above-mentioned agents with the compression agent.

The test is carried out over 21 days, during which the subjects consume two tablets after the three main meals, i.e. 6 tablets per day.

Three groups are formed, a control group A which consumes a placebo, a group B which consumes montmorillonite tablets, and a group C which consumes PVP+ montmorillonite tablets.

The measurement of the abdominal perimeter is done on days D1, D3, D5, D8, D10, D12, D15, D17 and D19, for the midday meal. For each day of evaluation, the measurement was done at the following times: H-1, H0) (time of talking of tablets), H0.25, H0.5, H1, and H1.5.

The results are expressed as an average change of the abdominal perimeter after the meals compared to H-1, in centimeters:

Group A: II0: + 1.5/II0.25: + 2.0/II0.5: + 1.9/II1: + 1.9/II1.5: + 1.3
Group B: H0: + 1.3/H0.25: + 1.3/H0.5: + 1.0/H1: + 0.9/H1.5: + 0.6
Group C: H0: + 1.2/H0.25: + 1.1/H0.5: + 1.0/H1: + 0.8/H1.5 + 0.5

The statistical analysis of these results shows that the difference existing between the placebo group and the two other groups is significant.

The tolerance to the treatment was:
GROUP A. no particular sensation
GROUP B: problems of constipation, especially the first week
GROUP C: no particular problem It is thus noted that the use of PVP associated with montmorillonite according to the present invention develops a synergy which promotes the reduction of the change in waistline after meal. Moreover, the use solves the problem of constipation met with clay.

EXAMPLE 4
PVP-Containing Chewing Gum

The test is carried out on two groups, a control group A, consuming normal chewing gums, and a group B which consumes chewing gums to which has been added Polyplasdone INF 10 at the concentration of 0.7 g for 100 g of chewing paste. One chewing gum is taken after each meal.

The test is carried out according to the following procedure:

| Week 1 |
| --- |
| day 1: group A: sensations of compression after meals |
| group B: nothing to report |
| day 2: control A: abdominal swelling after meals |
| group B: feeling of well-being after meals |
| day 3: control A: abdominal swelling after meals |
| group B: impression of a better stomach outline |

A pause for one week (7 days) is made, then the taking is reversed, the group A taking the product to which the PVP according to the present invention has been added, and the group B becoming the group Control B without PVP. The taking is always three chewing gums per day, one after each meal.

| Week 2 |
| --- |
| day 1: group A: nothing to report |
| group B: sensations of compression after meals |
| day 2: control A: feeling of well-being after meals |
| group B: abdominal swelling after meals |

Thus, the invention enables, once again, reducing the sensations of compression and swelling due to the in waistline and caused by eating ways.

What is claimed is:

1. A method of reducing abdominal swelling in a mammal, comprising delivering to a mammal in need thereof and substantially simultaneously with a meal an amount of polyvinylpyrrolidone or povidone effective to reduce or eliminate abdominal swelling resulting temporarily from the absorption of the meal.

2. A method of reducing abdominal swelling in a mammal, resulting temporarily from absorption of a meal, comprising delivering to a mammal in need thereof and substantially simultaneously with the meal at least one component having a secondary constipating effect, in combination with an amount of polyvinylpyrrolidone or povidone effective to reduce or eliminate appearance of said constipating effect from said at least one component.

3. The method of claim 1, wherein said polyvinylpyrrolidone has a molecular weight between 10,000 and more than 2.8 million.

4. The method of claim 2, wherein said polyvinylpyrrolidone has a molecular weight between 10,000 and more than 2.8 million.

5. The method of claim 1, wherein said polyvinylpyrrolidone has a molecular weight between 10,000 and more than 2.8 million and is selected from the group consisting of a soluble polyvinylpyrrolidone, an insoluble polyvinylpyrrolidone, a crosslinked polyvinylpyrrolidone, a non-crosslinked polyvinylpyrrolidone, a crosslinked soluble polyvinylpyrrolidone, a crosslinked insoluble polyvinylpyrrolidone, a non-crosslinked soluble polyvinylpyrrolidone and a non-crosslinked insoluble polyvinylpyrrolidone.

6. The method claim 2, wherein said polyvinylpyrrolidone has a molecular weight between 10,000 and more than 2.8 million and is selected from the group consisting of a soluble polyvinylpyrrolidone, an insoluble polyvinylpyrrolidone, a crosslinked polyvinylpyrrolidone, a non-crosslinked polyvinylpyrrolidone, a crosslinked soluble polyvinylpyrrolidone, a crosslinked insoluble polyvinylpyrrolidone, a non-crosslinked soluble polyvinylpyrrolidone and a non-crosslinked insoluble polyvinylpyrrolidone.

7. The method of claim 1, wherein the polyvinylpyrrolidone is present in the form of a composition to be absorbed separately from food.

8. The method of claim 2, wherein the polyvinylpyrrolidone is present in the form of a composition to be absorbed separately from food.

9. The method of claim 1, wherein said polyvinylpyrrolidone is directly incorporated in food.

10. The method of claim 2, wherein said polyvinylpyrrolidone is directly incorporated in food.

11. The method of claim 1, wherein the concentration of polyvinylpyrrolidone ranges between a homeopathic concentration and 100% by weight or by volume.

12. The method of claim 2, wherein the concentration of polyvinylpyrrolidone ranges between a homeopathic concentration and 100% by weight or by volume.

13. The method of claim 1, wherein the polyvinylpyrrolidone is formulated in association with at least one further active ingredient selected from the group consisting of an activated charcoal and a clay.

14. The method of claim 2, wherein the polyvinylpyrrolidone is formulated in association with at least one said constipating component selected from the group consisting of an activated charcoal and a clay.

15. The method of claim 1, wherein said clay is selected from the group consisting of montmorillonite, kaolinite, attapulgite, sepiolite, smectite and bentonite clay.

16. The method of claim 2, wherein said clay is selected from the group consisting of montmorillonite, kaolinite, attapulgite, sepiolite, smectite and bentonite clay.

17. The method of claim 1, wherein said polyvinylpyrrolidone is administered in an amount of at least $10^{-12}$ g.

18. The method of claim 4, wherein said polyvinylpyrrolidone is administered in an amount of at least $10^{-12}$ g.

19. The method of claim 1, wherein said polyvinylpyrrolidone is administered in an amount between $10^{-12}$ g and about 1 g per unit dose.

20. The method of claim 2, wherein said polyvinylpyrrolidone is administered in an amount between $10^{-12}$ g and about 1 g per unit dose.

21. The method of claim 1, wherein the polyvinylpyrrolidone is administered in an amount between $10^{-12}$ g and about 1 g for 100 g of products to be chewed or to be ingested.

22. The method of claim 2, wherein the polyvinylpyrrolidone is administered in an amount between $10^{-12}$ g and about 1 g for 100 g of products to be chewed or to be ingested.

* * * * *